(12) United States Patent
Lagerstedt

(10) Patent No.: US 6,177,048 B1
(45) Date of Patent: Jan. 23, 2001

(54) METHOD OF STERILIZING CONTAINERS BASED ON FIBER

(75) Inventor: Jan Lagerstedt, Malmö (SE)

(73) Assignee: Tetra Laval Holdings & Finance S.A., Pully (CH)

( * ) Notice: Under 35 U.S.C. 154(b), the term of this patent shall be extended for 0 days.

(21) Appl. No.: 09/269,570

(22) PCT Filed: Sep. 18, 1997

(86) PCT No.: PCT/SE97/01574

§ 371 Date: Mar. 30, 1999

§ 102(e) Date: Mar. 30, 1999

(87) PCT Pub. No.: WO98/16431

PCT Pub. Date: Apr. 23, 1998

(30) Foreign Application Priority Data

Oct. 16, 1996 (SE) .................................................. 9603782

(51) Int. Cl.[7] ....................................................... A23L 3/10
(52) U.S. Cl. ................. 422/26; 422/25; 422/33; 422/38; 426/407; 426/521; 53/425
(58) Field of Search ................... 422/25, 26, 28, 422/33, 38, 292, 295, 302, 307, 900; 53/425; 426/407, 521

(56) References Cited

U.S. PATENT DOCUMENTS

| 3,987,818 | * | 10/1976 | Champel | 422/26 |
| 4,296,067 | | 10/1981 | Nasman et al. | 422/26 |
| 4,497,773 | | 2/1985 | Kuelzow et al. | 422/26 |

* cited by examiner

*Primary Examiner*—Terrence R. Till
*Assistant Examiner*—Theresa T. Snider
(74) *Attorney, Agent, or Firm*—Burns, Doane, Swecker & Mathis, L.L.P.

(57) ABSTRACT

A method is described for sterilizing a fiber based container that contains a food product without damaging the container. The method involves placing the filled container in an autoclave, and supplying steam into the closed autoclave to raised the temperature to a sterilization temperature and at a pressure above atmospheric. The temperature required for sterilizing the food product is greater than the critical temperature for the container. The cooling phase involves introducing cooling air into the autoclave to reduce the temperature below the critical temperature without introducing moisture, and then supplying cool water to lower the temperature of the container rapidly. The use of this method provides effective sterilization in a reduced cycle time.

9 Claims, No Drawings

METHOD OF STERILIZING CONTAINERS BASED ON FIBER

This appln is a 371 of PCT/SE97/01574 Sep. 18, 1997.

TECHNICAL FIELD

The present invention relates to a method of sterilizing fibre-based containers. More specifically, the invention relates to a method in connection with autoclaving a fibre-based container, the cycle time of the sterilizing process being reduced.

BACKGROUND OF THE INVENTION

A heat treatment for killing and/or inactivation of microorganisms can be accomplished by means of moist as well as dry heat. In the food industry the heat treatment in moist heat is preferred since the biological killing and inactivating mechanisms are much more effective at a high water content than at a low water content, i.e. dry heat. Besides, the heat transfer in the equipment used for the heat treatment is much more effective with moist heat.

In a package material having a base layer of paper or board this layer must be made relatively thick in order to give the container a necessary dimensional rigidity. However, containers made of these laminates based on paper or board have the drawback of rapidly losing their mechanical strength properties when they are subjected to liquid or moisture, which results in that the container becomes flabby and cumbersome. Thus, such known containers made of a packaging laminate with a liquid absorbing fibre layer cannot be subjected to a heat treatment with moist heat without the desired mechanical rigidity of the packaging laminate and thus the dimensional stability of the container being impaired or lost.

In order to avoid these problems packaging laminates have been developed which are adapted to withstand drastic conditions in the form of moisture and/or heat. Such a known alternative package material has for example a strengthening base layer of plastic and a filler intermixed with the plastic. This material has proved to be less moisture sensitive than the previously used materials based on paper and board. Containers manufactured from these laminates are very suitable for preservation by means of refrigeration as well as heat. When a preservation by means of refrigeration is used these containers with a solid and/or liquid filling material can be chilled by means of water cooling.

However, paper and board are cheap package materials, and containers have thus been developed which comprise a laminate with a base layer of one of these materials. Containers manufactured from such a material of laminate type in the form of a sheet or a web can be heat treated in a humid atmosphere at high temperatures.

These laminates can by means of folding be used for the manufacture of dimensional stable impermeable packaging containers which are very suitable to be used at most extreme conditions in a humid environment including heat treatment with moist heat at an overpressure. Such harsh environments comprise autoclaving at temperatures and periods which are accepted for foods. This means that the laminate is also highly suitable to be used for the manufacture of a container which is intended to be filled with a food under aseptic conditions. In this connection the product is sterilized and filled under almost sterile conditions in a likewise sterilized container which after filling is sealed in such a way that the filled product during storage is not reinfected by microorganisms before it is consumed.

Such a heat treatment of the containers is achieved with a heat transfer medium containing water. Generally, a heat treatment with moist heat is utilized at overpressures in autoclaves which are filled with water or steam. In this connection an autoclaving cycle can be divided into a rise time, a holding time, and a cooling time. The rise time is the time from the beginning of the heating and until the desired temperature has been reached. At an overpressure of 0.5 bar the steam has a temperature of about 110° C., and at an overpressure of 1.1 bar the temperature becomes about 121° C. After the holding time, which is the time required to achieve a sterilization at the desired constant temperature, the pressure in the autoclave is lowered to a normal atmospheric pressure, and during the cooling time the temperature is lowered by means of cooling the autoclave.

Since autoclaving is a sterilization method which uses an overpressure this method is mostly performed as a batch procedure and not continuously. It is thus of interest to be able to reduce the cycle time when autoclaving.

However, it has become apparent that when the above-mentioned containers are too extensively heat treated they are subjected to environments whereby the good sealing properties of the containers against moisture and liquid partly are lost. Due to the soaking paper or board layers it is in this way a risk that the package material loses its mechanical strength properties and that the container becomes flabby and cumbersome. It is thus important that this type of containers is exposed to such environments to the smallest extent possible.

SUMMARY OF THE INVENTION

In order to solve the problems mentioned above, the method for sterilizing a fiber-based container filled with a food product according to the invention includes filling a fiber-based container with a food product, placing the filled container into an interior of an autoclave, supplying steam to the interior of the autoclave under pressure to maintain the interior of the autoclave at an overpressure of between about 0.5 and 1.1 bar, while maintaining th interior of the autoclave at a sterilization temperature for the food product for a predetermined period of time, cooling the interior of the autoclave by supplying a gas having a temperature less than the temperature of the gas in steam supply step, but greater than 70° C., thereby causing a reduction in the pressure in the autoclave, and cooling the filled container in the autoclave by discontinuing the supply of the gas and by supplying a cooling liquid to the interior of the autoclave.

A further aspect of the invention provides a method of sterilizing a fiber based container including providing a fiber-based container having a critical temperature for obtaining desired sealing properties, filling the fiber-based container with a food product, placing the filled container into an interior of an autoclave, supplying steam to the interior of the autoclave to increase the temperature in the autoclave to a predetermined temperature above the critical temperature, maintaining the interior of the autoclave at the predetermined temperature for a predetermined period of time, supplying a gas to the interior of the autoclave, the gas having a temperature less than the predetermined temperature to cool the interior of the autoclave, after cooling the interior of the autoclave to the critical temperature, discontinuing the supplying of gas, and beginning the supply of a cooling liquid to the interior of the autoclave, and removing the container from the autoclave.

DETAILED DESCRIPTION OF THE INVENTION

When sterilizing containers containing fibre the cooling of the containers has previously been effected with air in order to compensate for the problems mentioned above. However, it has been shown in connection with autoclaving that such containers with for example a soaking layer of paper or board very well tolerate heating up to a critical temperature as well as cooling with water in liquid phase as a heat transfer medium.

Different types of material require different process times and/or different times for heating/killing/cooling. Above all, the critical temperature depends on the thickness of the base layer and of the fibre content in its composition, but the other components of the packaging laminate are also of importance. Thus, the critical temperature varies between about 70° C. and about 95° C., preferably between about 80° C. and about 85° C. With a folded container manufactured from a material of the laminate type in the form of a sheet or a web, which material comprises a base layer, an outer coating and an inner coating, the critical temperature can be as high as about 90° C.

The sterilization of filled containers by means of autoclaving is carried out in a cyclic course. Such a cycle comprises the above mentioned phases following each other: rise time, holding time, and cooling time. The heat transfer medium can according to the invention be exchanged during the rise time and/or during the holding time. Since for example cooling with air is considerably slower than cooling with water a combined cooling procedure for containers which are based on fibre and which can be autoclaved, in which procedure the air is replaced with water-cooling, results in that a shorter cooling time is achieved. In the corresponding way a heating with steam is faster than to spray with water, which is a usual preheating method in connection with heat treating processes. Thus, such exchanges of the heat transfer medium improve the efficiency of the sterilizing cycle, and this in turn results in an improved process economy.

In this connection a heat transfer medium means an agent which transfers heat energy from or to the container. Suitable heat transfer media comprise for example water (in liquid phase), steam, and air. During the cooling of a container after the sterilization by means of for example autoclaving the heat transfer medium is according to the invention exchanged at the critical temperature, preferably from air to water. The cooling below the critical temperature can also be accomplished by means of spraying with cool water, if necessary with an accompanying cooling with $CO_2$ or $N_2$ in order to rapidly achieve a sufficiently low temperature. With this in view it is also possible to end the cooling phase with dry blowing. In the same way the heat transfer medium can be exchanged at the critical temperature during the heating of a container before autoclaving.

In summary, package materials exist which are exposed to environments requiring good sealing properties of the container against moisture and liquid. Above a certain critical temperature these materials can not completely withstand the negative effect of the water on the mechanical properties of the package material. Consequently, the containers are exposed to these non-favourable conditions as briefly as possible while maintaining the sterilization effect required. This is according to the invention achieved by the heat transfer medium used for heating and/or cooling of the container, respectively, being exchanged during the heating and/or cooling of the container at a critical temperature for the container when it is sterilized by means of heat treatment, preferably autoclaving. Preferably, the sterilization is performed in an autoclave, the temperature of which is allowed to rise to the autoclaving temperature suitable for the application, which temperature is maintained during a sufficient holding time. Then the container is cooled with a medium not containing water, which medium preferably is air, down to the critical temperature, at which temperature the medium is exchanged for water.

Calculations from experiments in practice have shown that the process time can be reduced considerably by means of this cycle of steam-air-water. In dependence of the type of container the cooling time can for example be shortened with about 10 minutes from earlier duration times of about 30–50 min.

I claim:

1. A method for sterilizing a fiber-based container filled with a food product comprising:
   (a) filling a fiber-based container with a food product;
   (b) placing the filled container in an interior of an autoclave;
   (c) supplying steam to the interior of the autoclave under pressure to maintain the interior of the autoclave at an overpressure of between about 0.5 and 1.1 bar, while maintaining the interior of the autoclave at a sterilization temperature for the food product for a predetermined period of time;
   (d) cooling the interior of the autoclave by supplying a gas having a temperature less than the sterilization temperature in step (c), but greater than 70° C., thereby causing a reduction in the pressure in the autoclave; and
   (e) cooling the filled container in the autoclave by discontinuing the supply of the gas and by supplying a cooling liquid to the interior of the autoclave.

2. The method according to claim 1, wherein the cooling gas is air.

3. The method according to claim 1, wherein the cooling liquid is water.

4. The method according to claim 1, wherein the sterilization temperature is between about 110° C. and about 121° C.

5. A method of sterilizing a fiber based container comprising:
   (a) providing a fiber-based container having a critical temperature for obtaining desired sealing properties;
   (b) filling the fiber-based container with a food product;
   (c) placing the filled container in an interior of an autoclave;
   (d) supplying steam to the interior of the autoclave to increase the temperature in the autoclave to a predetermined temperature above the critical temperature;
   (e) maintaining the interior of the autoclave at the predetermined temperature for a predetermined period of time;
   (f) supplying a gas to the interior of the autoclave, the gas having a temperature less than the predetermined temperature to cool the interior of the autoclave;
   (g) after cooling the interior of the autoclave to the critical temperature, discontinuing the supplying of gas, and beginning the supply of a cooling liquid to the interior of the autoclave; and
   (h) removing the container from the autoclave.

6. The method according to claim 5, wherein the critical temperature is between about 70° C. and about 95° C.

7. The method according to claim 5, wherein the predetermined temperature is about 110° C. at an overpressure of 0.5 bar in the autoclave.

8. The method according to claim 5, wherein the predetermined temperature is about 121° C. at an overpressure of 1.1 bar in the autoclave.

9. The method according to claim 5, wherein the predetermined temperature and the predetermined time are sufficient to effect sterilization of the food product in the container.

* * * * *